(12) United States Patent
Zhong et al.

(10) Patent No.: US 6,322,847 B1
(45) Date of Patent: *Nov. 27, 2001

(54) MEDICAL DEVICE COATING METHODS AND DEVICES

(75) Inventors: Sheng-ping Zhong, Northborough; Vladimir B. Tsukernik, West Roxbury, both of MA (US)

(73) Assignee: Boston Scientific, Inc., Natick, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/685,641

(22) Filed: Oct. 10, 2000

Related U.S. Application Data (63) Continuation of application No. 09/303,860, filed on May 3, 1999, now Pat. No. 6,156,373.

(51) Int. Cl.$^7$ .............................. A61L 33/00; B05D 3/04; B05D 3/02; B05D 7/22
(52) U.S. Cl. .................. 427/2.28; 427/2.3; 427/348; 427/378; 427/232; 427/235
(58) Field of Search ..................... 427/2.28, 2.3, 427/348, 378, 232, 235, 2.25, 421, 430.1, 2.24

(56) References Cited

U.S. PATENT DOCUMENTS

| | | | |
|---|---|---|---|
| 3,946,125 | 3/1976 | Scheiber | 427/46 |
| 4,391,797 | 7/1983 | Folkman et al. | 424/19 |
| 4,459,317 | 7/1984 | Lambert | 427/2 |

(List continued on next page.)

FOREIGN PATENT DOCUMENTS

| | | |
|---|---|---|
| 0 274 846 B1 | 7/1988 | (EP) . |
| 0 294 905 A1 | 12/1988 | (EP) . |
| 0 470 246 B1 | 2/1992 | (EP) . |

(List continued on next page.)

OTHER PUBLICATIONS

Bartoli et al., "In Vitro and in Vivo Antitumoral Activity of Free, and Encapsulated Taxol", *J. Macroencapsulation*, vol. 7, No. 2 (1990) pp. 191–197.

Bruck. Stephen, "Interactions of Synthetic and Natural Surfaces with Blood in the Physiological Environment," *J. Biomed. Materi. Res. Symposium*, No. 8 (1977) pp. 1–21.

Cox, David A., M.D. et al., "Effect of Local Delivery of Heparin and Methotrexate on Neointimal Proliferation in Stented Porcine Coronary Arteries", *Coronary Artery Disease*, vol. 3, No. 3, Mar. 1992, pp. 237–248.

(List continued on next page.)

*Primary Examiner*—Shrive P. Beck
*Assistant Examiner*—Jennifer Kolb
(74) *Attorney, Agent, or Firm*—Pennie & Edmonds LLP (57) ABSTRACT

Devices and methods for applying a polymeric coating to a medical device. The steps of the coating process including applying a liquid polymeric material to the surface of the medical device, then directing a stream of gas to impinge on the surface of the medical device. Excess liquid polymeric material is removed from the surface of the medical device. The devices used in the coating process and the coated medical device are also part of this invention.

18 Claims, 7 Drawing Sheets

U.S. PATENT DOCUMENTS

| | | | |
|---|---|---|---|
| 4,487,808 | 12/1984 | Lambert | 428/423.1 |
| 4,768,507 | 9/1988 | Fischell et al. | 128/303 R |
| 4,770,664 | 9/1988 | Gogolewski | 623/66 |
| 4,842,575 | 6/1989 | Hoffman, Jr. et al. | 600/36 |
| 4,923,464 | 5/1990 | DiPisa, Jr. | 606/195 |
| 4,969,890 | 11/1990 | Sugita et al. | 606/192 |
| 4,994,071 | 2/1991 | MacGregor | 606/194 |
| 5,019,096 | 5/1991 | Fox, Jr. et al. | 623/1 |
| 5,092,885 | 3/1992 | Yamada et al. | 623/11 |
| 5,102,402 | 4/1992 | Dror et al. | 604/265 |
| 5,102,417 | 4/1992 | Palmaz | 606/195 |
| 5,192,308 * | 3/1993 | Ostapchenko | 623/1 |
| 5,222,971 | 6/1993 | Willard et al. | 606/158 |
| 5,258,202 | 11/1993 | Pellegrino et al. | 427/235 |
| 5,282,823 | 2/1994 | Schwartz et al. | 606/198 |
| 5,304,121 | 4/1994 | Sahatjian | 604/53 |
| 5,324,261 | 6/1994 | Amundson et al. | 604/96 |
| 5,370,614 | 12/1994 | Amudson et a l. | 604/96 |
| 5,380,299 | 1/1995 | Fearnot et al. | 604/265 |
| 5,383,928 | 1/1995 | Scott et al. | 623/1 |
| 5,419,760 | 5/1995 | Narciso, Jr. | 604/8 |
| 5,423,885 | 6/1995 | Williams | 623/1 |
| 5,443,458 | 8/1995 | Eury | 604/891.1 |
| 5,443,496 | 8/1995 | Schwartz et al. | 623/1 |
| 5,447,724 | 9/1995 | Helmus et al. | 424/426 |
| 5,449,372 | 9/1995 | Schmaltz et al. | 606/198 |
| 5,449,382 | 9/1995 | Dayton | 623/1 |
| 5,464,650 | 11/1995 | Berg et al. | 427/2.3 |
| 5,512,055 | 4/1996 | Domb et al. | 604/265 |
| 5,514,154 | 5/1996 | Lau et al. | 606/195 |
| 5,527,337 | 6/1996 | Stack et al. | 606/198 |
| 5,545,208 | 8/1996 | Wolff et al. | 623/1 |
| 5,562,922 | 10/1996 | Lambert | 424/486 |
| 5,569,463 | 10/1996 | Helmus et al. | 424/426 |
| 5,578,075 | 11/1996 | Dayton | 623/1 |
| 5,591,227 | 1/1997 | Dinh et al. | 623/1 |
| 5,605,696 | 2/1997 | Eury et al. | 424/423 |
| 5,609,629 | 3/1997 | Fearnot et al. | 623/1 |
| 5,611,151 * | 3/1997 | Jacob | 34/395 |
| 5,616,608 | 4/1997 | Kinsella et al. | 514/449 |
| 5,624,411 | 4/1997 | Tuch | 604/265 |
| 5,626,862 | 5/1997 | Brem et al. | 424/426 |
| 5,635,201 | 6/1997 | Fabo | 424/443 |
| 5,637,113 | 6/1997 | Tartaglia et al. | 623/1 |
| 5,651,986 | 7/1997 | Brem et al. | 424/484 |
| 5,674,192 | 10/1997 | Sahatjian et al. | 604/28 |
| 5,674,241 | 10/1997 | Bley et al. | 606/198 |
| 5,674,242 | 10/1997 | Phan et al. | 606/198 |
| 5,679,400 | 10/1997 | Tuch | 427/2.14 |
| 5,697,697 | 12/1997 | Dinh et al. | 623/1 |
| 5,700,286 | 12/1997 | Tartaglia et al. | 623/1 |
| 5,702,754 | 12/1997 | Zhong | 427/2.12 |
| 5,709,874 | 1/1998 | Hanson et al. | 424/423 |
| 5,712,326 | 1/1998 | Jones et al. | 523/105 |
| 5,716,981 | 2/1998 | Hunter et al. | 514/449 |
| 5,733,925 | 3/1998 | Kunz et al. | 514/449 |
| 5,739,237 | 4/1998 | Russell et al. | 526/277 |
| 5,755,769 | 5/1998 | Richard et al. | 623/11 |
| 5,776,184 | 7/1998 | Tuch | 623/1 |
| 5,779,732 | 7/1998 | Amundson | 606/198 |
| 5,824,361 * | 10/1998 | Asanuma | 427/127 |
| 5,837,008 | 11/1998 | Berg et al. | 623/1 |
| 5,958,512 | 9/1999 | Krish et al. | 427/338 |
| 6,156,373 | 12/2000 | Zhong et al. | 427/2.28 |

FOREIGN PATENT DOCUMENTS

| | | | |
|---|---|---|---|
| 0 470 569 A1 | 2/1992 | (EP) | |
| 0 543 653 A1 | 5/1993 | (EP) | |
| 0 551 182 A1 | 7/1993 | (EP) | |
| 0 562 752 A1 | 9/1993 | (EP) | |
| 0 567 816 A1 | 11/1993 | (EP) | |
| 0 568 310 A1 | 11/1993 | (EP) | |
| 0 604 022 A1 | 6/1994 | (EP) | |
| 0 623 354 A1 | 11/1994 | (EP) | |
| 0 706 376 B1 | 4/1996 | (EP) | |
| 0 707 897 A1 | 4/1996 | (EP) | |
| 0 562 752 A1 * | 3/1993 | (EP) | B05D/1/18 |
| 2 696 527 A1 | 4/1994 | (FR) | |
| WO 92/15286 A1 | 9/1972 | (WO) | |
| WO 90/01969 A1 | 3/1990 | (WO) | |
| WO 90/13332 A1 | 11/1990 | (WO) | |
| WP 91/07154 A1 | 5/1991 | (WO) | |
| WO 91/10424 A1 | 7/1991 | (WO) | |
| WO 91/11193 A1 | 8/1991 | (WO) | |
| WO 91/12779 A1 | 9/1991 | (WO) | |
| WO 92/00747 A1 | 1/1992 | (WO) | |
| WO 92/12717 A2 | 8/1992 | (WO) | |
| WO 93/06792 A1 | 4/1993 | (WO) | |
| WO 93/11120 A1 | 6/1993 | (WO) | |
| WO 94/21308 A1 | 9/1994 | (WO) | |
| WO 95/03795 A1 | 2/1995 | (WO) | |
| WO 96/03092 A1 | 2/1996 | (WO) | |
| WO 96/03984 A1 | 2/1996 | (WO) | |
| WO 96/25176 A1 | 8/1996 | (WO) | |
| WO 96/26689 A1 | 9/1996 | (WO) | |
| WO 98/36784 A1 | 8/1998 | (WO) | |
| WO 00/04999 * | 2/2000 | (WO) | B05C/3/09 |

OTHER PUBLICATIONS

Cox, D. A. et al., "Local Delivery of Heparin and Methotrexate Fails to Inhibit in Vivo Smooth Muscle Cell Proliferation", *Supplement to Circulation Abstracts From the 64$^{th}$ Scientific Sessions*, vol. 84, No. 4. Abstract No. 0284, 1991, p. II–71.

Dev. V. et al., "Kinetics of Drug Delivery to the Arterial Wall Via Polyurethane Coated Removable Nitinol Stent–Comparative Study of 2 Drugs", *Circulation Abstracts From the 66$^{th}$ Scientific Sessions*, vol. 88, No. 4, Part 2, Abstract No. 1657 (1993) p. I–3.

Esquivel, Carlos O., M.D. et al., "Reduced Thrombogenic Characteristics of Expanded Polytetrafluoroethylene and Polyurethane Arterial Grafts After Heparin Bonding," *Surgery*, vol. 95, No. Jan. 1984, pp. 102–107.

Guyton, John R. et al., "Inhibition of Rat Arterial Smooth Muscle Cell Proliferation by Heparin." *Circulation Research*, vol. 46, No. 5, May 1980, pp. 625–634.

Jampel, Henry D., M.D. et al., "In Vitro Release of Hydrophobic Drugs From Polyanhydride Disks", *Ophthalmic Surgery*, dated prior to Jan. 8, 1991.

Kawahito, Kohi et al., "Heparin Coated Percutaneous Cardiopulmonary Support for the Treatment of Circulatory Collapse After Cardiac Surgery," *ASAIO Journal*, vol. 40, No. 4, Oct.–Dec. 1994, pp. 972–976.

Kishida, Akio et al., "Immobilization of Human Thrombomodulin onto Biomaterials," *ASAIO Journal* (1994) pp. M840–M845.

Lambert, T. et al., "A New Method For Arterial Drug Delivery Via Removable Stent", *JACC*, vol. 21, No. 2, Abstract No. 834-2 (1993) P. 483A.

Lambert, T. et al., "Localized Arterial Drug Delivery From a Polymer Coated Removable Metallic Stent: Kinetics and Bioactivity of Forskolin", *Circulation Abstracts From the $66^{th}$ Scientific Sessions*, vol. 88, No. 4, Part 2, Abstract No. 1659 (1993) p. I–3.

Lindhardt, Robert J. et al., "Differential Anticoagulant Activity of Heparin Fragments Prepated Using Microbial Heparinase," *The Journal of Biological Chemist*, vol. 257, No. 13, Issue of Jul. 10, pp. 7310–7313.

Miyama, Hajime et al., "New Antithrombogenic Heparinized Polymer," *J. Biomed Mater. Res.*, vol. 11 (1977) pp. 251–265.

Moses, Marsha A. et al., *Inhibitors of Angiogenesis*, Review, The Children's Hosptial Medical Center, Boston, MA, dated prior to Jan. 8, 1999.

Nichols, Allen B., M.D. et al., "Effect of Heparin Bonding on Catheter–Induced Fibrin Formation and Platelet Activation," *Circulation*, vol. 70, No. 5, Nov. 1984, pp. 843–850.

"A Powerful Case For LOPID", Parke–Davis, dated prior to Jan. 8, 1999.

Pitt, C.G. et al., "The Design of Controlled Drug Delivery Systems Based on Biodegredable Polymers", *Progress in Contraceptive Delivery Systems*, M T P Press, Lancaster, vol. 1 (1980) pp. 17–18.

Sheppeck, Richard A. et al., "Examination of the Roles of Glycoprotein Ib and Glycoprotein IIb/IIIa in Platelet Deposition on an Artificial Surface Using Clinical Antiplatelet Agents and Monoclonal Antibody Blockade," *Blood*, vol. 78, No. 3, Aug. 1, 1991, pp. 673–680.

Tang, Chris et al., "Regression of Collagen–Induced Arthritis with Taxol, A Microtubule Stabilizer", *Arthritis Rheum.*, vol. 36, No. 9 (Suppl.) (1993) p. 42.

Whitborne, Richard, Ph.D., Presentation at the $2^{nd}$ International Coronary Stenting Summit (Mar. 1–2 1991).

* cited by examiner

MEDICAL DEVICE COATING METHODS AND DEVICES

This application is a continuation of pending U.S. patent application Ser. No. 09/303,860, filed May 3, 1999, now U.S. Pat. No. 6,156,373.

FIELD OF THE INVENTION

The present invention relates generally to a medical device having a surface treatment applied over a portion of its surface. More particularly, the present invention relates to implantable medical devices having drug release coatings including a therapeutic substance in a polymeric carrier.

BACKGROUND OF THE INVENTION

There are a number of medical conditions which may be effectively treated with implantable medical devices. In many cases, the therapeutic effect of the implantable medical device may be enhanced, if the device includes a drug release coating including a therapeutic substance in a polymeric carrier. Two examples of implantable medical devices which may include such drug release coatings are endovascular stents and vascular filters.

Intravascular diseases are commonly treated by relatively non-invasive techniques such as percutaneous transluminal angioplasty (PTA) and percutaneous transluminal coronary angioplasty (PTCA). These angioplasty techniques typically involve the use of a guidewire and a balloon catheter. In these procedures, a balloon catheter is advanced over a guidewire such that the balloon is positioned proximate a restriction in a diseased vessel. The balloon is then inflated and the restriction in the vessel is opened.

While angioplasty techniques have gained wide acceptance, abrupt closure and restenosis have been identified as possible subsequent occurrences. Abrupt closure refers to the acute occlusion of a vessel immediately after or within the initial hours following a dilation procedure. Abrupt closure can result in myocardial infarction if blood flow is not restored in a timely manner. The primary mechanisms of abrupt closures are arterial dissection and/or thrombosis. Restenosis refers to the re-narrowing of an artery after an initially successful angioplasty. Restenosis occurs primarily within the initial six months after angioplasty, and is believed due to the proliferation and migration of the cellular components of the arterial wall.

Endovascular stents are placed in the dilated segment of a vessel lumen to mechanically block the effects of abrupt closure and restenosis. Such a stent is disclosed in U.S. Pat. No. 5,514,154 to Lau et al.

Recent developments have led to stents which can provide anti-thrombogenic and other medications to regions of a blood vessel which have been treated by angioplasty or to other interventional techniques. In U.S. Pat. No. 5,464,650, Berg et al. disclose a method for making an intravascular stent by applying to the stent, and in particular to its tissuecontacting surface, a solution which includes a solvent, a polymer dissolved in the solvent, and a therapeutic substance dispersed in the solvent. After the solution is applied to the stent, the solvent is evaporated leaving the polymer/therapeutic agent surface treatment. Berg et. al. assert that these devices are capable of providing both short term medication delivery, over the initial hours and days after treatment, as well as long term medication delivery, over the weeks and months after treatment.

The process disclosed by Berg et al., which uses a polymeric carrier, is prone to the formation of polymeric surface imperfections during the coating process. This is especially evident on stents, which generally include many wire like members with interstitial spaces therebetween. The surface imperfections can include strands of drug laden polymeric material hanging loosely from or extending across the interstitial spaces in the stent. The imperfections can also include chunks or thickened coating portions at particular points relative to the rest of the coating. These imperfections, because of their drug delivering capabilities, may cause adverse effects. Loose strands or strands across interstitial spaces may not be secure, and thus, may enter the blood stream and fail to provide local treatment. If these agents are released to locations other than the targeted area, unwanted side effects may result. An uneven coating may also result in non-uniform treatment of the vessel wall.

As mentioned previously, vascular filters are another type of implantable medical device which may benefit from the inclusion of a drug release coating including a therapeutic substance in a polymeric carrier. One of the most common applications for vascular filters is the treatment of Deep Venous Thrombosis (DVT). Deep Venous Thrombosis patients experience clotting of blood in the large veins of the lower portions of the body. These patients are constantly at risk of a clot breaking free and traveling via the inferior vena cava to the heart and lungs. This process is known as pulmonary embolization. Pulmonary embolization can frequently be fatal, because large blood clots can interfere with the function of the heart and/or lungs. For example, a large blood clot which becomes trapped proximate the heart may interfere with the life-sustaining pumping action of the heart. A blood clot which passes through the heart will be pumped into the lungs and may cause a blockage in the pulmonary arteries. A blockage of this type in the lungs will interfere with the oxygenation of the blood causing shock or death.

Pulmonary embolization may be successfully prevented by the appropriate placement of a vascular filter in the vascular system of a patient's body. Placement of the filter may be accomplished by performing a laparotomy with the patient under general anesthesia. However, intravenous insertion is often the preferred method of placing a vascular in a patient's vascular system.

In the treatment of Deep Venous Thrombosis, a vascular filter is placed in the inferior vena cava of a patient. The inferior vena cava is a large vessel which returns blood to the heart from the lower part of the body. The inferior vena cava may be accessed through the patient's femoral vein.

Vascular filters may be placed in other locations when treating other conditions. For example, if blood clots are expected to approach the heart and lungs from the upper portion of the body, a vascular filter may be positioned in the superior vena cava. The superior vena cava is a large vessel which returns blood to the heart from the upper part of the body. The superior vena cava may by accessed through the jugular vein, located in the patient's neck. Once placed inside a blood vessel, a vascular filter acts to catch and hold blood clots. The flow of blood around the captured clots allows the body's lysing process to dissolve the clots.

SUMMARY OF THE INVENTION

The present invention pertains to implantable medical devices having drug release coatings including a therapeutic substance in a polymer carrier. The present invention provides a method of applying a coating to an implantable medical device which is evenly distributed over all of the surfaces of the device. Two examples of implantable medical devices which may be coated using this process are stents and thrombosis filters. This method of coating may also be used with other implantable medical devices. Also, this coating method may be used with stents of both self-expanding and balloon expandable designs.

Stents are normally comprised of a skeletal frame which includes openings and a lumen which extends longitudinally through the stent. A variety of processes are known for fabricating stents. A stent may consist of a plurality of filaments or fibers which are wound or braided together to form a continuous structure. Alternately, the skeletal frame of a stent may be formed by removing material from a tubular element using a laser cutting process. A stent may be comprised of any biocompatible material possessing the structural and mechanical attributes necessary for supporting a diseased vessel.

Often, it is beneficial to both stent and treat a localized area of a diseased vessel. A therapeutic agent, therefore, can be incorporated into a polymer and applied to the stent as a polymeric surface treatment. Incorporation of a therapeutic agent into a surface treatment greatly enhances the scope of this medical device by transforming the stent into a drug delivery system. Drugs and treatments which utilize anti-thrombogenic agents, antiangiogenisis agent, anti-proliferative agents, growth factors and radio chemicals may be readily deployed from within the matrix of the polymer surface treatment.

The application of such a surface treatment is generally accomplished by applying a coating solution to the stent. Typically, this coating solution includes a solvent, a polymer dissolved in the solvent and a therapeutic substance dispersed in the solvent. The coating solution may be applied to the stent using a variety of methods. For example, the solution may be applied to the stent by immersing the stent in liquid coating solution. Alternately, the coating solution may be applied to the stent with a brush. Finally, in a preferred embodiment, the coating solution may be sprayed onto the stent.

Solvent selection is critical to a functioning surface treatment. It is essential that the solvent is capable of placing the polymer into solution and that the solvent and polymer chosen do not materially alter the therapeutic character of the therapeutic agent. On the other hand, the therapeutic agent needs only to be dispersed throughout the solvent. The therapeutic agent, therefore, may be either in a true solution with the solvent or dispersed in fine particles within the solvent.

It is preferred that the polymeric coating be evenly distributed over the stent. Although the procedures for applying a polymeric surface treatments are optimized, they still often leave polymeric fibers, polymeric particles, or other polymeric surface aberrations or imperfections on the stent. These aberrations or imperfections in the polymeric coating may take on numerous sizes and shapes. Regardless of the application process utilized, several types of imperfections are common. Examples of these imperfections are polymeric fibers, which span across the openings of the skeletal framework of the stent, and lumps created by an overabundance of polymeric material in a localized area. Imperfections in the polymeric coating may be a result of disproportionate application of the coating solution, or the settling of excessive material in a particular location. At a minimum, the imperfections are unsightly. More importantly, imperfections may create adverse secondary effects.

The adverse secondary effects which may arise are correlated to the type of polymeric imperfections. Polymeric fibers are prone to two adverse effects; the fibers may dislodge from the stent, or they may release their therapeutic agents into the blood stream. Because fibers span across openings in the skeletal framework of the stent, they are attached typically at few locations. Expansion of the stent may dislodge these imperfections sending them into the circulatory system. At this point, there exists no control over the drug delivery capabilities of these rogue fibers. The release of drugs in undesired locations is likely to cause secondary effects. On the other hand, polymeric fibers may remain attached to the stent. Some of the fibers which remain attached to the stent may not engage the wall of the blood vessel. In this instance, the entire surface of the polymeric fibers is free to release therapeutic agent directly into the blood stream, causing other secondary effects.

Polymeric lumps are caused by an overabundance of polymeric material in a localized area, these lumps may also cause secondary effects. As mentioned above, the goal of applying a polymeric surface treatment to a stent is to have uniform coverage and uniform release of a therapeutic substance. When there are areas of excess coverage on the stent, the targeted diseased tissue may receive a non-uniform dosage of the released therapeutic agent. For therapeutic agents, especially ones which promote or restrict endothelial cell growth, uneven release may cause non-optimal treatment. Another problem created by polymeric lumps is that the lumps may be in a location of the stent where they do not contact the wall of the blood vessel. In this instance, the entire surface area of the lumps will be free to release therapeutic agent directly into the blood stream, causing other secondary effects.

The present invention provides a method of applying an even coating to an implantable medical device either alone or in a combination with a therapeutic substance. The process begins with the step of preparing a coating solution preferably including a polymer, a solvent, and a therapeutic substance. The coating solution is then applied to the stent by dipping, spraying or any other acceptable method. A tool or assembly as described herein is then used to direct a gas stream so that the gas stream impinges on the surfaces of the stent. When the gas from the gas stream strikes the surfaces of the stent, it displaces excess coating solution. The tool or assembly may be moved to direct the gas stream at the stent from a plurality of different locations and from a plurality of different angles. The tool or assembly may also be in continuous rotational motion such that the gas streams generally impinge across the entire circumference of the stent. The tool may be adapted so that it may be passed through the entire lumen of the stent. The flow of gas through the openings and around the wires of the stent is sufficient to displace excess coating solution, any lumps, fibers, etc. formed by the coating solution and will be blown off the surfaces of the stent by the gas stream. Once the excess coating solution has been removed from the surfaces of the stent, the solvent of the coating solution is allowed to evaporate, thereby leaving on the surface of the stent, a polymer coating. As described above, the polymer coating ideally includes a therapeutic agent. Because all imperfections were removed before the coating solution was allowed to dry, the polymer coating which results from this process was evenly distributed across the surface of the stent.

It should be understood that the coating method described above may be used in conjunction with any stent design. For example, this coating method may be used with both self-expanding and balloon expandable stents. The coating method described above may also be used with implantable medical devices other than stents. For example, a thrombosis filter may be coated using a coating method described above.

A typical thrombosis filter includes a body member and a plurality of elongated struts. Each strut has a free end and a joined end. The joined end of each strut is fixably attached to the body member. The struts radiate outwardly from the body member such that the thrombus filter is generally conical in shape. When the thrombosis is deployed inside a blood vessel, the free ends of the struts engage the blood vessel wall. The body member of the thrombosis filter is held in a position proximate the center of the blood vessel by the plurality of struts which engage the blood vessel walls with opposing force vectors.

The walls of the blood vessel are lined with a thin inner membrane or intima. When the free ends of the thrombus filter disrupt this inner membrane, the body responds in a process known as neointimal hyperplasia, or endothelial growth. As a result of this process, the disrupted area of the inner membrane is overgrown with a number of new cells. The free ends of the thrombosis filter struts are encapsulated with new cell growth within 2–3 weeks of the implant of the filter.

Due to endothelial growth, thrombus filters placed in the blood vessel of a patient become affixed in the blood vessel walls within 2–3 weeks after being implanted. Because the free ends of the thrombus filter struts contacting the blood vessel walls become fixed in this way, many thrombosis filters cannot be removed percutaneously after being in place for more than two weeks. Applying a polymer coating including a therapeutic substance in a polymer carrier to the free ends of a vascular filter struts may assist in preventing or reducing endothelial growth proximate the free ends of the struts.

When the thrombosis filter is disposed in a blood vessel, the conical formation of struts acts to trap or capture blood clots. The generally conical shape of the formation of struts serves to urge captured blood clots toward the center of the blood flow. The flow of blood around the captured blood clots allows the body's natural lysing process to dissolve the clots. Applying a polymer coating including a therapeutic substance in a polymeric carrier to the vascular filter may assist the body in dissolving blood clots.

The present invention provides a method which may be used to apply an evenly distributed polymeric coating to an implantable medical device such as a thrombus filter. The process begins with the step of preparing a coating solution preferably including a polymer, a solvent, and a therapeutic substance. The coating solution is then applied to selected surfaces of the thrombus filter. A tool or assembly is then used to direct gas streams so that they impinge on the surfaces of the thrombus filter. When the gas of the gas streams strikes the surfaces of the thrombus filter, it displaces excess coating solution. To assure that the gas streams impinge upon substantially all of the surfaces of the thrombus filter, the tool may be rotated or moved in a linear direction. The tool or assembly may also be moved to a variety of positions. The flow of gas around the struts and body member of the thrombus filter is sufficient to displace excess coating solution. Once the excess coating solution has been removed from the surfaces of the thrombosis filter, the solvent in the coating solution is allowed to evaporate thereby leaving on the surface of the thrombosis filter a polymer coating which preferably includes a therapeutic agent. Because all imperfections were removed before the solvent was allowed to evaporate, the polymer coating resulting from this process is evenly distributed across the surfaces of the thrombosis filter.

DETAILED DESCRIPTION OF THE INVENTION

The following detailed description should be read with reference to the drawings, in which like elements in different drawings are numbered identically. The drawings which are not necessarily to scale, depict selected embodiments and are not intended to limit the scope of the invention.

Examples of constructions, materials, dimensions, and manufacturing processes are provided for selected elements. All other elements employ that which is known to those of skill in the field of the invention. Those skilled in the art will recognize that many of the examples provided have suitable alternatives which may be utilized.

Figure 1:
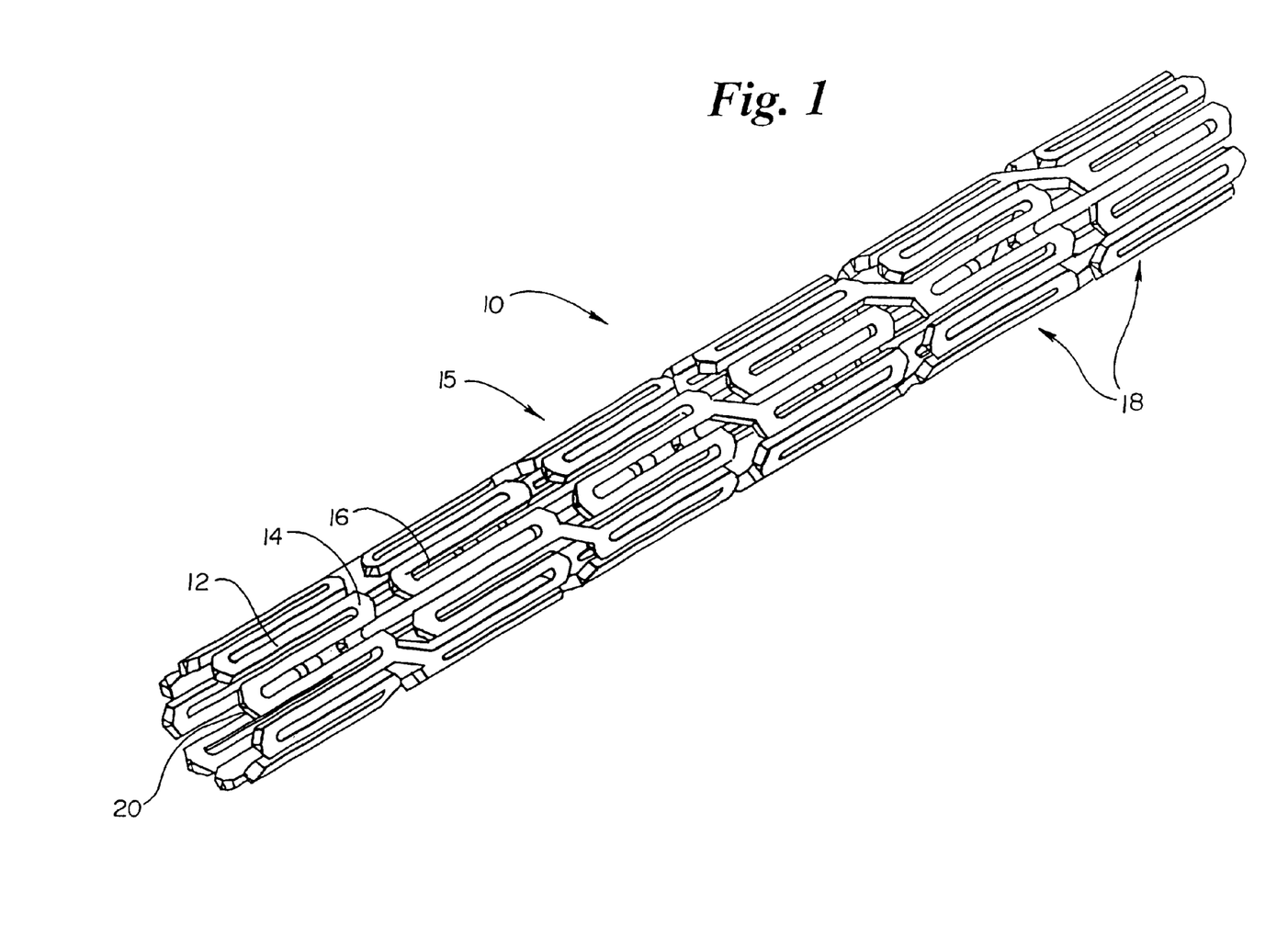
FIG. 1 is a perspective view of a stent in accordance with an exemplary embodiment of the present invention.

FIG. 1 is a perspective view of a stent 10 having a skeletal frame 15. Skeletal frame 15 of stent 10 includes wire-like members or struts 12 forming a distinct, repetitive serpentine pattern. This repetitive serpentine pattern includes multiple U-shaped curves 14. Skeletal frame 15 also includes a plurality of openings or apertures 16. With no recognizable beginning or end to this serpentine pattern, each wire 12 forms an expandable serpentine element 18. Serpentine elements 18 are arranged along the longitudinal axis of stent 10 so that abutting serpentine elements 18 may be joined together with additional wires 12. Skeletal frame 15 substantially forms a lumen 20 extending longitudinally through stent 10.

The term "wire", as used in describing the material of skeletal frame 15 should not be mistaken as being limited to metallic materials. In fact, the "wire" forming stent 10 may be comprised of any biocompatible material possessing the structural and mechanical attributes necessary for supporting a diseased vessel. Thus, both metallic and non-metallic materials are suitable. Examples of preferred biocompatible metallic materials include stainless steel, tantalum, gold, titanium, and nickel-titanium alloy. Preferred non-metallic materials may be selected from the following list, which is not exhaustive: poly(L-lactide) (PLLA), poly(D,L-lactide) (PLA), polyglycolide (PGA), poly(L-lactide-co-D,L-lactide) (PLLA/PLA), poly(L-lactide-co-glycolide) (PLLA/PGA), poly(D, L-lactide-co-glycolide) (PLA/PGA), poly (glycolide-co-trimethylene carbonate) (PGA/PTMC), polyethylene oxide (PEO), polydioxanone (PDS), polycaprolactone (PCL), polyhydroxylbutyrate (PHBT), poly (phosphazene), polyD,L-lactide-co-caprolactone) (PLA/PCL), poly(glycolide-co-caprolactone) (PGA/PCL), polyanhydrides (PAN), poly(ortho esters), poly(phoshate ester), poly(amino acid), poly(hydroxy butyrate), polyacrylate, polyacrylamid, poly(hydroxyethyl methacrylate), polyurethane, polysiloxane and their copolymers.

Skeletal frame 15 of stent 10 may be formed through various methods. For example, skeletal frame 15 may be assembled from a plurality of wires 12 joined together by welding or soldering. Skeletal frame 15 may be molded in one piece using an injection molding process. Skeletal frame 15 may also be comprised of a plurality of filaments or fibers which are wound or braided together to form a continuous structure. Finally, in a preferred embodiment, skeletal frame 15 may be formed by removing material from a tubular element using a LASER cutting process.

Often it is beneficial to both stent and treat a localized area of a diseased vessel. A therapeutic agent, therefore, can be incorporated into a polymer and applied to stent 10 as a polymeric surface treatment. The incorporation of a therapeutic agent into a surface treatment greatly enhances the scope of this medical device by transforming the stent into a drug-delivery system. Drugs and treatments which utilize anti-thrombogenic agents, antiangiogenisis agents, anti-proliferative agents, growth factors, and radiochemicals may be readily deployed from within the matrix of the polymeric surface treatment. Specific examples of preferred therapeutic agents include angiopeptin, colchicine, lovastatin, trapidil, ticlopidine, hirudin, Taxol, and heparin. Specific examples of growth factors which may serve as therapeutic agents include VEGF, TGF-beta, IGF, PDGF, and FGF.

The application of such a surface treatment is generally accomplished by applying a coating solution to stent 10 . Typically, this coating solution includes a solvent, a polymer dissolved in the solvent, and a therapeutic substance dispersed in the solvent. The coating solution may be applied to stent 10 using a variety of methods. For example, the solution may be applied to stent 10 by immersing stent 10 in the coating solution. Alternately, the coating solution may be applied to stent 10 with a brush. Finally, in a preferred embodiment, the coating solution may be sprayed onto stent 10. Airbrushes suitable for spraying a solution of this type are commercially available from Badger Air-Brush of Franklin Park Ill.

Solvent selection is critical to a functioning surface treatment. It is essential that the solvent is capable of placing the polymer into solution, and that the solvent and polymer chosen do not materially alter the therapeutic character of the therapeutic agent. On the other hand, the therapeutic agent needs only to be dispersed throughout the solvent. The therapeutic agent, therefore, may be either in a true solution with the solvent or dispersed in fine particles within the solvent.

Examples of some suitable polymer/solvent/therapeutic agent combinations can include: polylactic acid/trichloroethane/colchicine; polyurethane/tetrahydrofuron/Taxol; (PLA/PCL)/dimethylformamide/hirudin; (PLA/PGA)/ethylacetate/ticlopidine; and polyethylene oxide/ethanol/heparin. It should be understood that these combinations are merely exemplary, and it is recognized that other combinations are possible.

Figure 2:
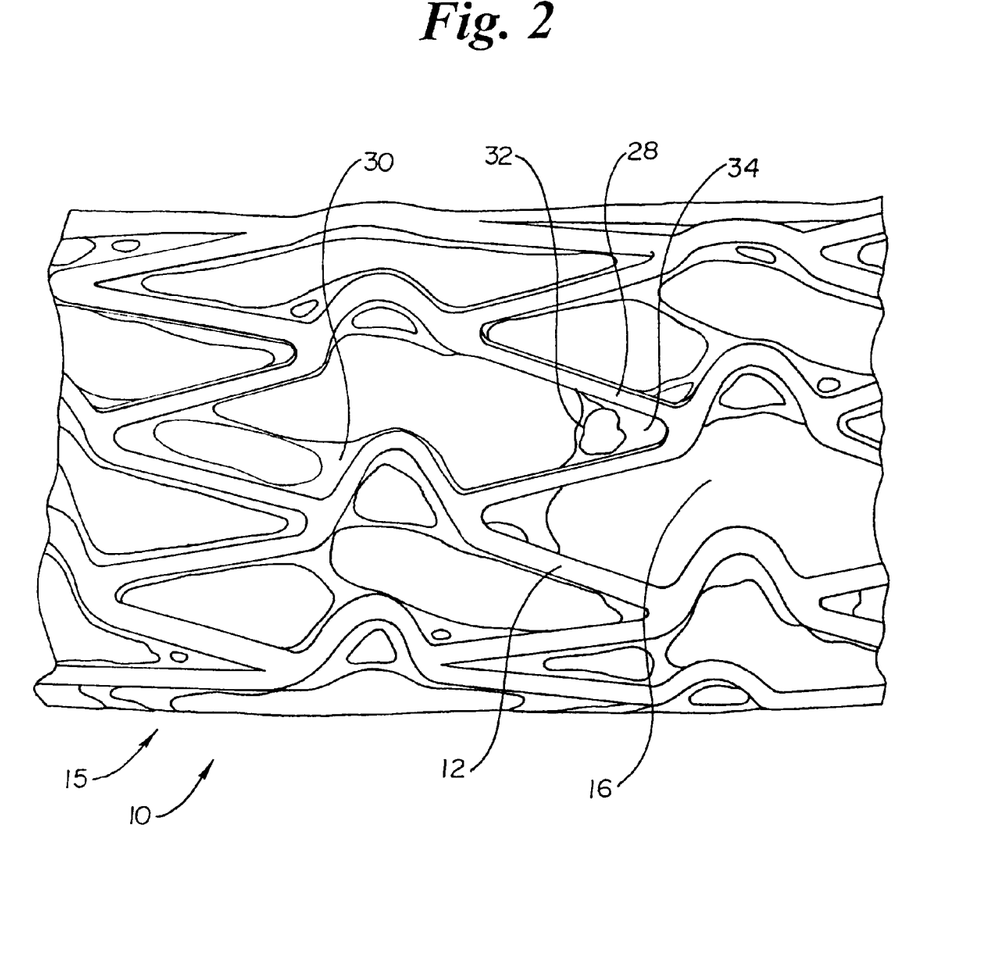
FIG. 2 is a magnified, partial plan view of the stent of FIG. 1, illustrating the polymeric surface aberrations and imperfections arising from a polymeric coating procedure.

FIG. 2 shows a magnified, partial plan view of stent 10, including wires 12 and openings 16. The surfaces of stent 10 are covered with a polymeric coating 28. Polymeric coating 28 is created by applying a solution preferably including polymer, solvent, and therapeutic agent to the surfaces of stent 10 then allowing the solvent to evaporate, thereby leaving on the stent surface a coating of the polymer and the therapeutic agent. A number of processes may be used to apply the coating solution to stent 10, including spraying, dipping, brushing, etc.

It is preferred that polymeric coating 28 be evenly distributed over stent 10. Although the procedures for applying the polymeric surface treatments are optimized, they still often leave polymeric fibers, polymeric particles, or other polymeric surface aberrations or imperfections on stent 10. These aberrations or imperfections in polymeric coating 28 are illustrated in FIG. 2. Polymeric imperfections 30 may take on numerous shapes and sizes. Regardless of the application process utilized, several types of imperfections 30 are common. Examples of these imperfections 30 are polymeric fibers 32 which span the openings 16 of the skeletal framework 15, and lumps 34 created by an overabundance of polymeric material in one location. Imperfections 30 in polymeric coating 28 may be the result of disproportionate application of the coating solution, or the settling of excessive material in a particular location. At a minimum, imperfections 30 are unsightly. More importantly, however, imperfections 30 may create adverse secondary effects.

The adverse secondary effects which may arise are cor-related to the type of polymeric imperfections 30. Polymeric fibers 32 are prone to two adverse effects; fibers 32 may dislodge from stent 10 or they may release their therapeutic agents into the blood stream. Because polymeric fibers 32 span across openings 16 of stent 10, they are attached typically at few locations. Expansion of stent 10 may dislodge these imperfections 32, sending them within the circulatory system. At this point, there exists no control over the drug delivering capabilities of these rogue fibers 32. The release of drugs in undesired locations is likely to cause secondary effects. On the other hand, polymeric fibers 32 may remain attached to stent 10. Some of the polymeric fibers 32 which remain attached to stent 10 may not engage the wall of the blood vessel. In this instance, the entire surface area of these polymeric fibers 32 is free to release therapeutic agent directly into the blood stream, causing other secondary effects.

Polymeric lumps 34 caused by an overabundance of polymeric material in a localized area may also cause secondary effects. As mentioned above, the goal of applying a polymeric surface treatment upon a stent 10 is to have uniform coverage and uniform release of a therapeutic substance. When there are areas of excess coverage on stent 10, the targeted diseased tissue may receive a non-uniform dosage of the released therapeutic agent. For therapeutic agents, especially ones which promote or restrict endothelial cell growth, uneven release may cause non-optimal treatment. Another problem created by lumps 34 is that the lumps 34 may be in a location on stent 10 where they do not contact the wall of the blood vessel. In this instance, the entire surface area of the lumps 34 will be free to release therapeutic agent directly into the blood stream, causing other secondary effects.

Figure 3:
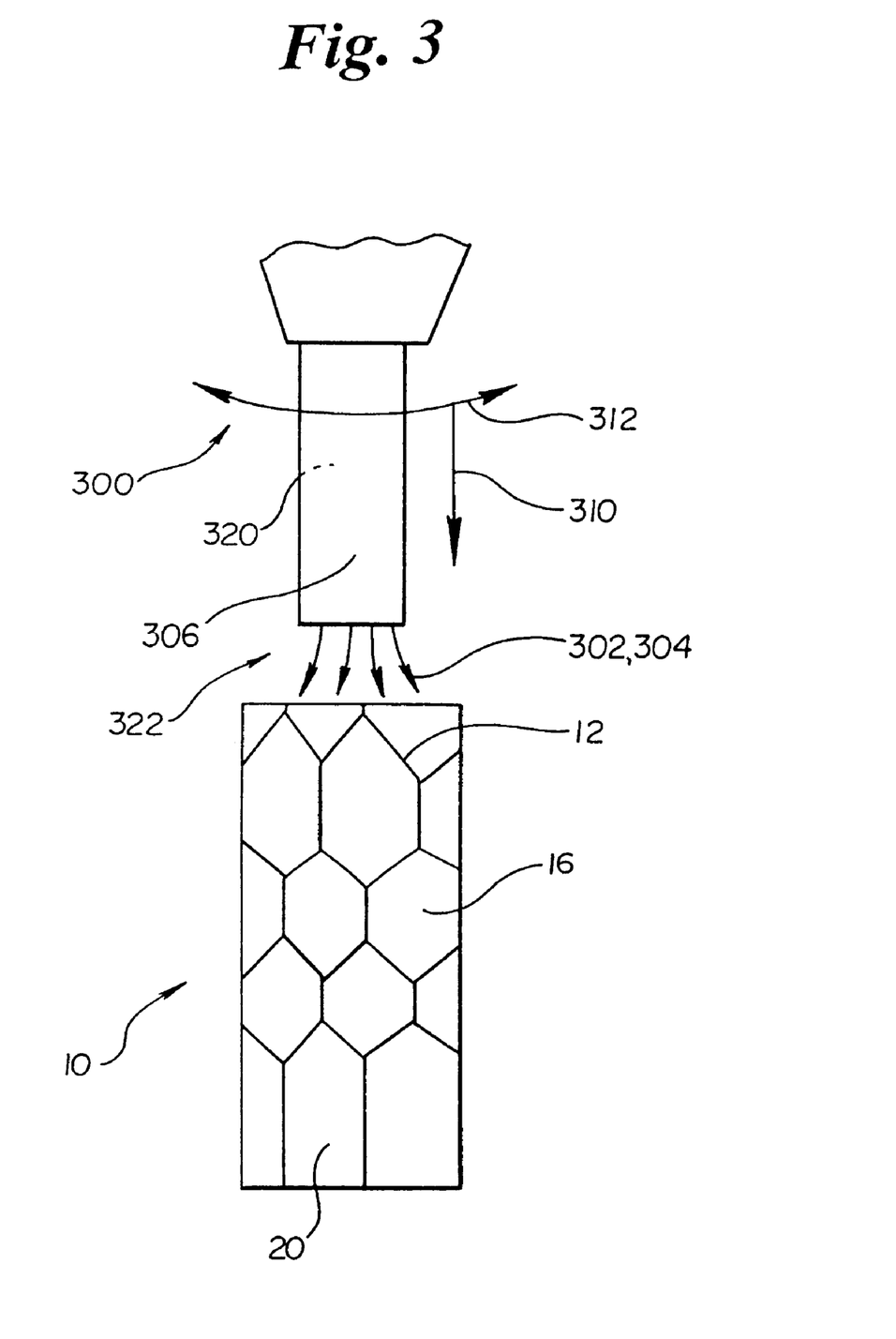
FIG. 3 is a plan view of a stent and an assembly to direct a gas stream at the stent surface.

FIG. 3 is a plan view of a stent 10 and a tool 300. As described previously, stent 10 includes wires 12, openings 16, and a lumen 20. A stream 302 of a gas 304 is shown exiting tool 300. In a preferred embodiment, tool 300 includes a generally tubular member 306 having a lumen extending therethough which is open at a distal end 322. The outer diameter of tubular member 306 is selected so that distal end 322 of tool 300 may readily enter lumen 20 of stent 10. A number of materials may be used to fabricate tool 300 including metallic and non-metallic materials. In a preferred embodiment, tool 300 is fabricated from hypodermic tubing. Hypodermic tubing is preferred because it is readily available with an appropriate outer diameter.

Tool 300 is in fluid communication with a supply (not shown) of compressed gas 304. Compressed gas 304 is preferably compressed air because it is inexpensive and readily available. Other gasses 304 may be used without departing from the spirit and scope of this invention. For example, acceptable results may be obtained using helium, nitrogen, argon, and carbon dioxide. Other gases may also be suitable for this application, including gasses which are not normally present in air. Compressed gas 304 is released to atmosphere through tool 300 to create stream 302.

Tool 300 may be moved as indicated by a direction vector 310 in FIG. 3. When tool 300 is moved in the direction indicated by vector 310, tool 300 is made to enter lumen 20 of stent 10. Tool 300 may also be rotated as illustrated by direction vector 312, to change the angle at which stream 302 strikes the surfaces of stent 10.

Tool 300 of FIG. 3 may be used in conjunction with a method of applying a polymer coating 28 to stent 10. The process begins with the step of preparing a coating solution preferably including a polymer, a solvent, and a therapeutic substance. The coating solution is then applied to the stent by dipping, spraying, or any other acceptable method. Tool 300 is then used to direct gas stream 302 so that it impinges on the surfaces of stent 10. When gas 304 of gas stream 302 strikes the surfaces of stent 10 it displaces excess coating solution.

Tool 300 may be moved to direct gas stream 302 at stent 10 from a plurality of different locations and from a plurality of different angles. For example, tool 300 may be moved as shown by vector 310 so that tool 300 passes partially or completely through lumen 20 of stent 10. Tool 300 may also be rotated as shown by vector 312 so that gas stream 302 strikes stent 10 at a plurality of angles. The position of tool 300 relative to stent 10 may also be changed without deviating from the spirit and scope of the invention.

The flow of gas 304 through openings 16 and around wires 12 is sufficient to displace excess coating solution. Any lumps, fibers, etc. formed by the coating solution will be blown off the surfaces of stent 10 or distributed more evenly over such surfaces by gas stream 302. Once the excess coating solution has been removed from or redistributed on the surfaces of stent 10, the remaining solution on the stent which is still liquid generally distributes evenly across the surface of the stent 10. The solvent in the coating solution is then allowed to evaporate thereby leaving on the surfaces of stent 10 a polymer coating 28. As described above, polymer coating 28 ideally includes a therapeutic agent. Because all imperfections were removed before the coating solution was allowed to dry, the polymer coating 28 resulting from this process is evenly distributed across the surfaces of stent 10.

Figure 4:
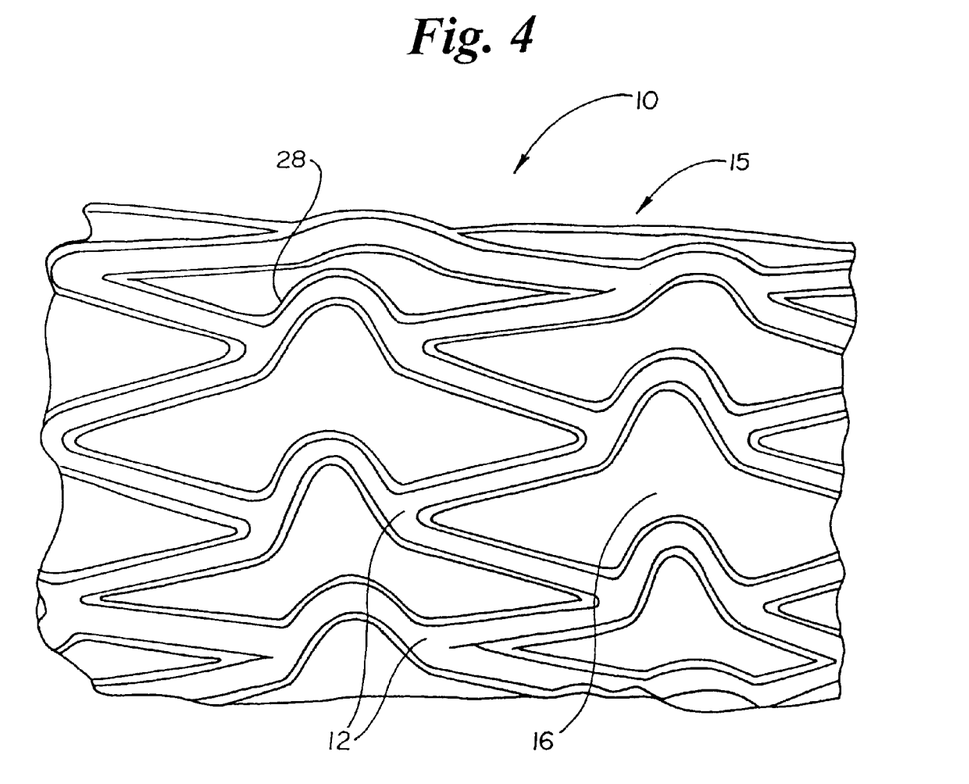
FIG. 4 is a magnified, partial plan view of the stent of FIG. 1, illustrating an evenly applied polymeric coating applied using the coating and surface treating method of the present invention.

FIG. 4 shows a magnified, partial plan view of stent 10, including wires 12 and openings 16. A polymeric coating 28 has been applied to stent 10 of FIG. 4 using the method described above. A coating solution including polymer, solvent, and therapeutic agent is applied to stent 10, excess coating was removed from stent 10, and the remaining solution on the stent which is still generally liquid, distributes evenly across the surface of the stent. The solvent was allowed to evaporate, thereby leaving on the stent surface a coating of the polymer and the therapeutic agent. As seen in FIG. 4, the resulting polymer coating is evenly distributed across the surfaces of stent 10. As described previously, polymeric coating 28 includes a polymer and a therapeutic agent, in a preferred embodiment. In an alternate embodiment, polymeric coating 28 may be comprised of a polymer.

Figure 5:
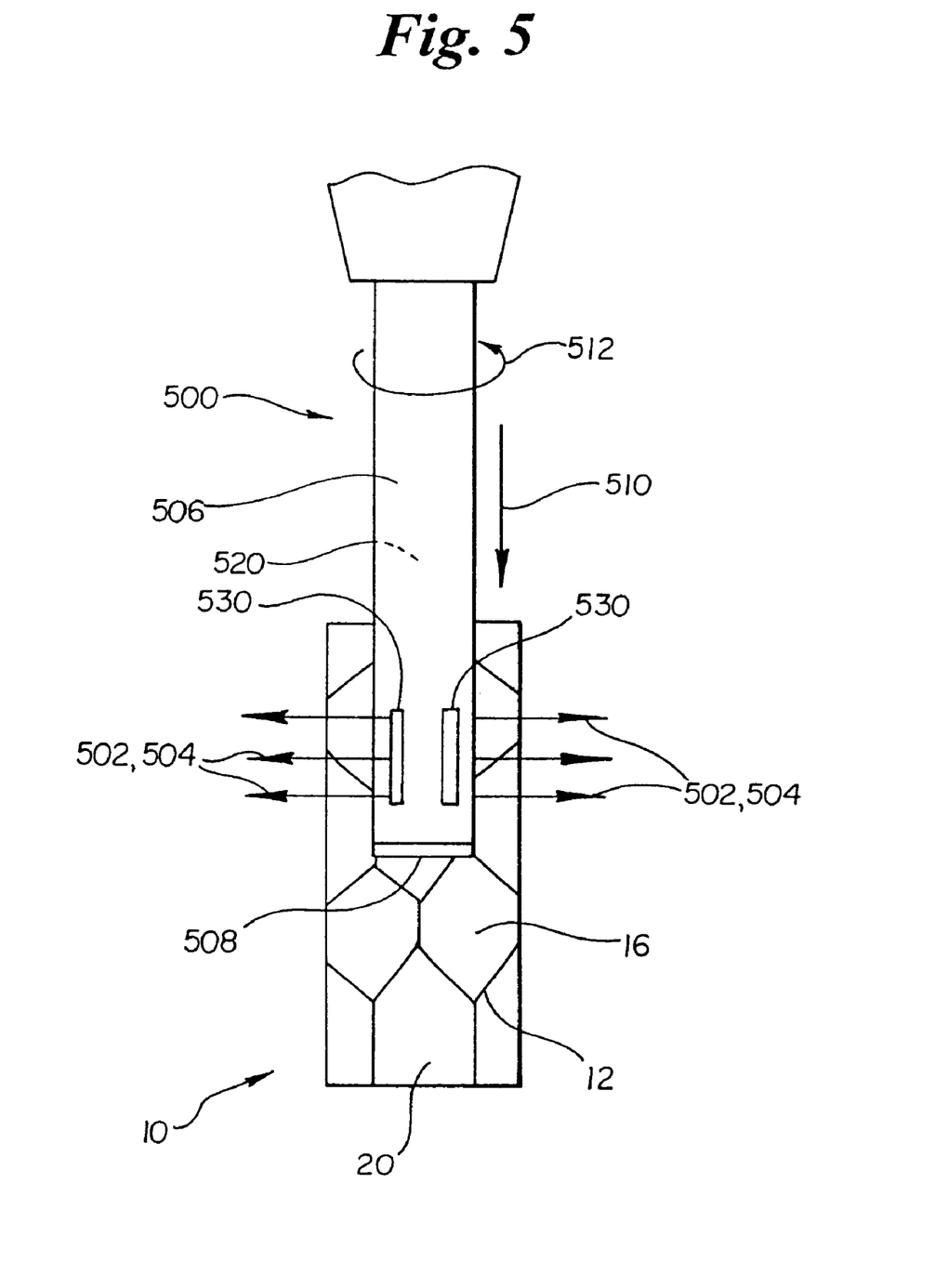
FIG. 5 is a plan view of a stent and an alternate assembly for directing a gas stream at the stent surface.

FIG. 5 is a plan view of a stent 10 and an alternate tool 500. As described previously, stent 10 includes wires 12, openings 16, and a lumen 20. A plurality of gas streams 502 are shown exiting tool 500. In a preferred embodiment, tool 500 includes a tubular member 506 and an end cap 508. Tubular member 506 includes a lumen 520 and a plurality of apertures 530. Apertures 530 provide a fluid passage from lumen 520 of tubular member 506 to the atmosphere surrounding tubular member 506. Although apertures 530 are illustrated as slots in FIG. 5, it should be understood that other embodiments of apertures 530 are possible without deviating from the spirit and scope of the invention. For example, apertures 530 may be round holes.

Tool 500 is in fluid communication with a supply (not shown) of compressed gas 504. The compressed gas 504 is released to atmosphere through tool 500 to create streams 502. Tool 500 may be moved as indicated by a direction vector 510 in FIG. 5. In this manner, tool 500 may be moved through lumen 520 of stent 10, so that streams 502 may be passed along the entire length of stent 10. Tool 500 may also be rotated as illustrated by direction vector 512. Rotating tool 500 allows streams 502 to pass across the entire circumference of stent 10.

Tool 500 of FIG. 5 may be used in conjunction with a method of applying a polymer coating 28 to stent 10. The process begins with the step of preparing a coating solution preferably including a polymer, a solvent, and a therapeutic substance. The coating solution is then applied to the stent by dipping, spraying, or any other acceptable method. Tool 500 is then used to direct gas streams 502 so that they impinge on the surfaces of stent 10. When gas 504 of gas streams 502 strikes the surfaces of stent 10 it displaces excess coating solution.

During this process, tool 500 may be rotated and moved in a linear direction. For example, tool 500 may be in continuous rotary motion as indicated by vector 512, such that streams 502 generally impinge on the entire circumference of stent 10. By way of a second example, tool 500 may be moved in a linear direction, so that streams 502 pass across the entire length of stent 10. It should be understood that tool 500 may be moved in a manner different than that shown in the above examples without deviating from the spirit and scope of the invention.

The flow of gas 504 through openings 16 and around wires 12 is sufficient to displace excess coating solution (e.g. any lumps, fibers, etc. formed by the coating solution will be blown off the surfaces of stent 10 by gas streams 502). Once the excess coating solution has been removed from or redistributed on the surfaces of stent 10, the remaining liquid solution generally distributes evenly over the stent surface 10. The solvent in the coating solution is allowed to evaporate thereby leaving on the surfaces of stent 10 a polymer coating 28, which preferably includes a therapeutic agent. Because all imperfections were removed before the coating solution was allowed to dry, the polymer coating 28 resulting from this process is evenly distributed across the surfaces of stent 10.

Figure 6:
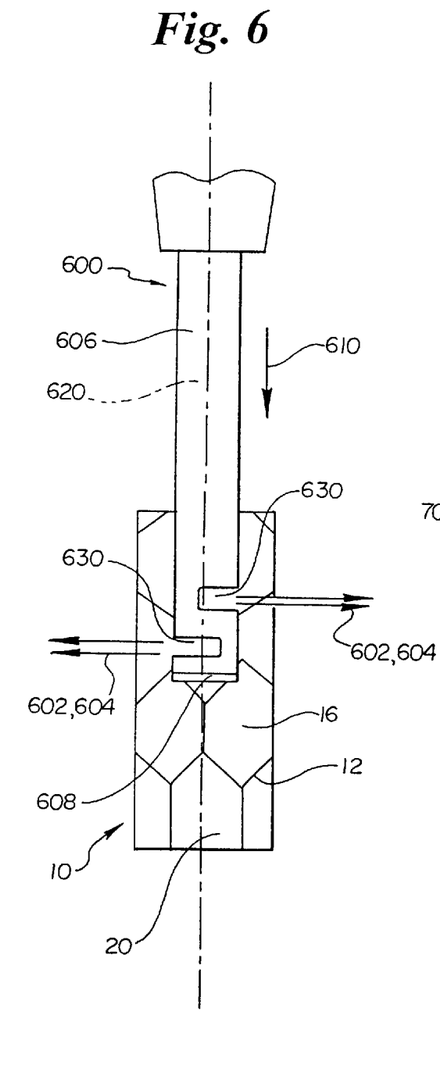
FIG. 6 is a plan view of a stent and another alternate assembly for directing a gas stream at the stent surface.

FIG. 6 is a plan view of a stent 10 and a tool 600. As described previously, stent 10 includes wires 12, openings 16, and a lumen 20. A plurality of gas streams 602 are shown exiting tool 600. In a preferred embodiment, tool 600 includes a tubular member 606 and an end cap 608. Tubular member 606 includes a lumen 620 and a plurality of apertures 630. Apertures 630 provide a fluid passage from lumen 620 of tubular member 606 to the atmosphere surrounding tubular member 606. In the embodiment of FIG. 6, apertures 630 are slots which are generally perpendicular to the axis of tubular member 606. As seen in FIG. 6, apertures 630 extend beyond the center of tubular member 606.

Lumen 620 of tool 600 is in fluid communication with a supply (not shown) of compressed gas 604. Compressed gas 604 is released to atmosphere through apertures 630 in tool 600 to create streams 602. As described above, the embodiment of FIG. 6 includes apertures 630 which are slots extending beyond the center of tubular member 606. As seen in FIG. 6, apertures 630 are adapted so that streams 602 of gas 604 may exit tool 600 along its entire circumference. This arrangement of apertures 630 creates a 360° pattern of streams 602 around tool 600.

Tool 600 may be moved as indicated by a direction vector 610 in FIG. 6. When tool 600 is moved in the direction indicated by vector 610, tool 600 is made to travel through lumen 20 of stent 10.

Tool 600 of FIG. 6 may be used in conjunction with a method of applying a polymer coating 28 to stent 10. The process begins with the step of preparing a coating solution preferably including a polymer, a solvent, and a therapeutic substance. The coating solution is then applied to the stent by dipping, spraying, or any other acceptable method. Tool 600 is then used to direct gas streams 602 so that they impinge on the surfaces of stent 10. When gas 604 of gas streams 602 strikes the surfaces of stent 10 it displaces excess coating solution. Tool 600 may be moved during this process to assure that gas streams 602 impinge upon substantially all the surfaces of stent 10.

The flow of gas 604 through openings 16 and around wires 12 is sufficient to displace excess coating solution (e.g. any lumps, fibers, etc. formed by the coating solution will be blown off the surfaces of stent 10 by gas streams 602). Once the excess coating solution has been removed from the surfaces of stent 10, the remaining liquid solution on the stent distributes evenly across the surface of the stent 10. The solvent in the coating solution is allowed to evaporate thereby leaving on the surfaces of stent 10 a polymer coating 28, which preferably includes a therapeutic agent. Because all imperfections were removed before the coating solution was allowed to dry, the polymer coating 28 resulting from this process is evenly distributed across the surfaces of stent 10.

Figure 7:
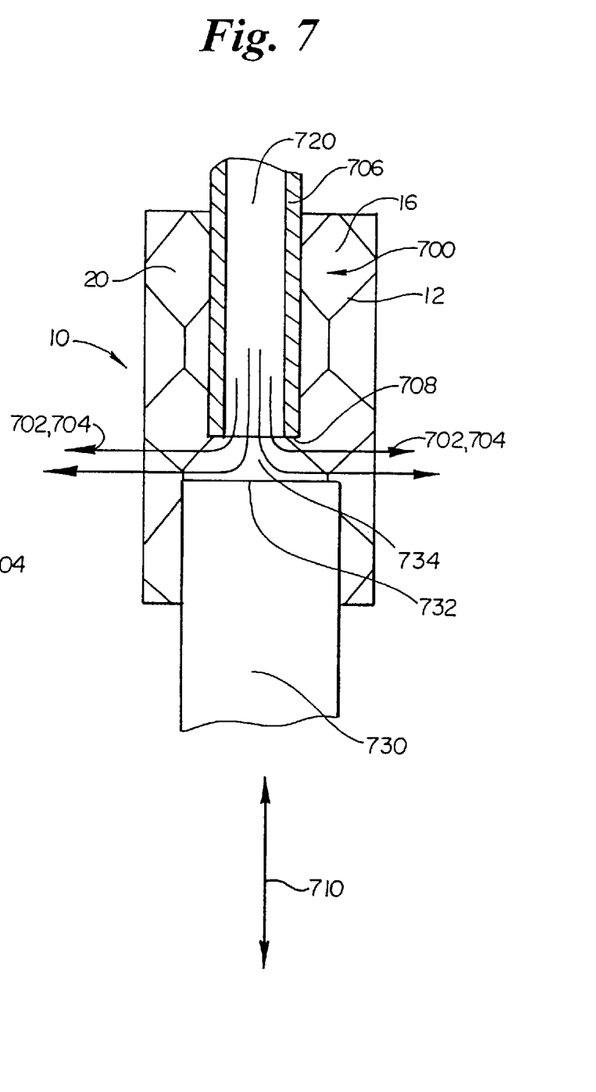
FIG. 7 is a plan view of a stent and a further alternate assembly for directing a gas stream at the stent surface.

FIG. 7 is a plan view of a stent 10, a tool 700, and a mandrel 730. As described previously, stent 10 includes wires 12, openings 16, and a lumen 20. Tool 700 is similar to the tool of FIG. 3 being a generally tubular member having a lumen therethrough which is open at one end. A stream 702 of a gas 704 is shown exiting tool 700. In a preferred embodiment, tool 700 includes a tubular member 706 having a lumen 720 and a distal end 708. Mandrel 730 is positioned so that its distal end 732 is proximate distal end 708 of tubular member 706 creating a narrow fluid passage 734. The aperture size of tool 700 may be varied by altering the position of the mandrel 730 relative to the distal end of tubular member 706. This will control the size and force of the gas stream impinging on the stent 10 with the gas jet being uniform over the entire circumference of the stent.

Tool 700 is in fluid communication with a supply (not shown) of compressed gas 704. The compressed gas 704 is released to atmosphere through tubular member 706 and narrow fluid passage 734. When gas 704 exits narrow fluid passage 734 it is traveling in a direction which will cause it to impinge on the surfaces of stent 10.

Tool 700 and mandrel 730 may be moved as indicated by a direction vector 710 in FIG. 7. When tool 700 and mandrel 730 are moved in the direction indicated by vector 710, tool 700 and mandrel 730 may be made to pass through lumen 20 of stent 10.

Tool 700 and mandrel 730 of FIG. 7 may be used in conjunction with a method of applying a polymer coating 28 to stent 10. The process begins with the step of preparing a coating solution preferably including a polymer, a solvent, and a therapeutic substance. The coating solution is then applied to the stent by dipping, spraying, or any other acceptable method. Tool 700 and mandrel 730 are then used to direct gas stream 702 so that it impinges on the surfaces of stent 10. When gas 704 of gas stream 702 strikes the surfaces of stent 10 excess coating solution is displaced. Tool 700 and mandrel 730 may be moved during this process to assure that gas stream 702 impinges upon substantially all the surfaces of stent 10.

The flow of gas 704 through openings 16 and around wires 12 is sufficient to displace excess coating solution (e.g. any lumps, fibers, etc. formed by the coating solution will be blown off the surfaces of stent 10 by gas stream 702). Once the excess coating solution has been removed from or redistributed on the surfaces of stent 10, remaining liquid solution generally distributes evenly across the surface of the stent 10. The solvent in the coating solution is allowed to evaporate thereby leaving on the surfaces of stent 10 a polymer coating 28, which preferably includes a therapeutic agent. Because all imperfections were removed before the coating solution was allowed to dry, the polymer coating 28 resulting from this process is evenly distributed across the surfaces of stent 10.

It should be understood that the coating method described above may be used in conjunction with any stent design. For example, this coating method may be used with both self-expanding and balloon expandable stents. The coating method described above may also be used with implantable medical devices other than stents. For example, a thrombosis filter may be coated using the coating method described above.

Figure 8:
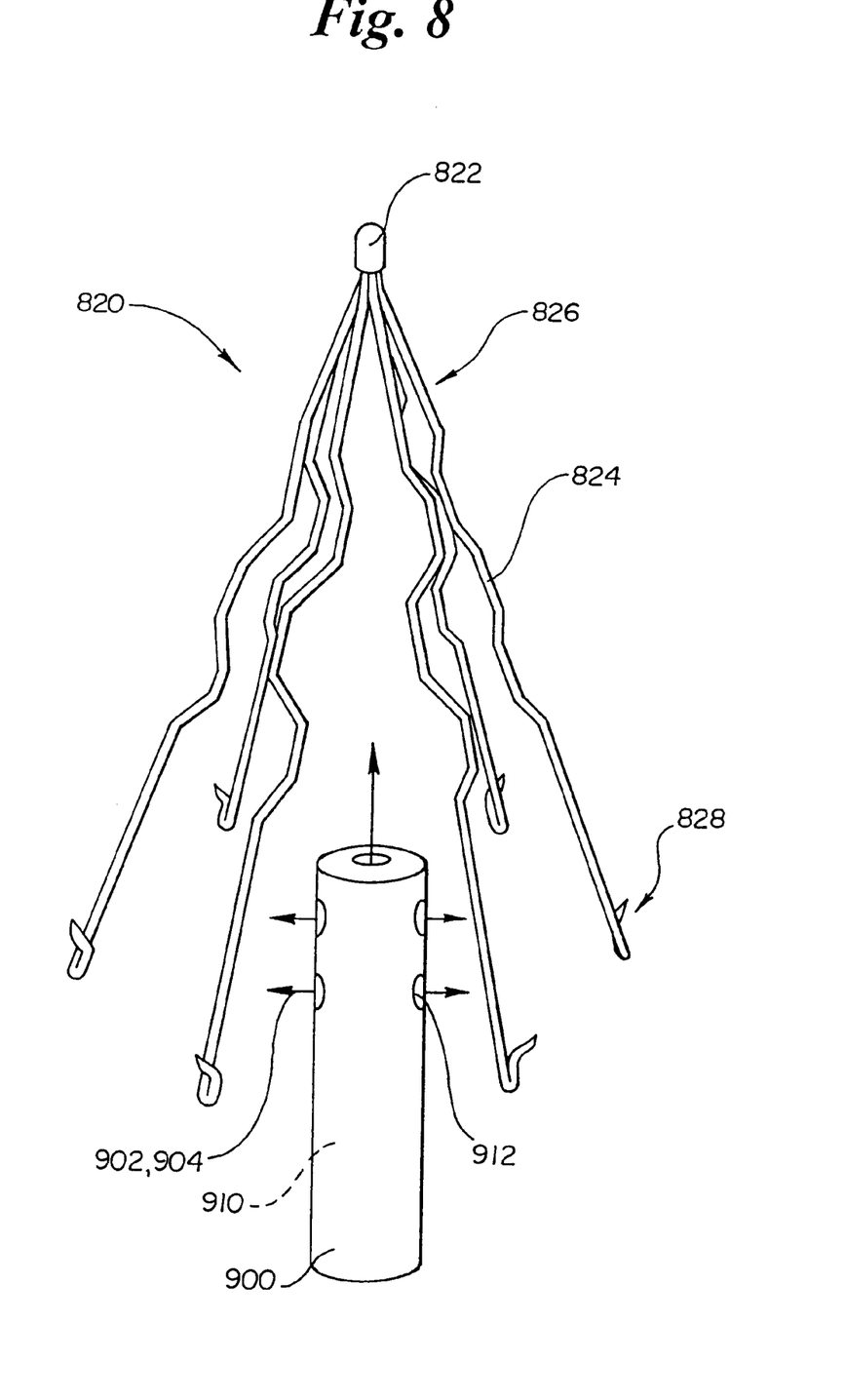
FIG. 8 is a perspective view of a thrombosis filter and an assembly for directing a gas stream at the filter surface.

FIG. 8 is a perspective view of a thrombosis filter 820. Thrombosis filter 820 includes a body member 822 and a plurality of elongated struts 824. Struts 824 each having a joined end 826 and a free end 828. Joined end 826 of each strut 824 is fixedly attached to body member 822.

Struts 824 may be comprised of any biocompatible material possessing the structural and mechanical attributes necessary to retain thrombus filter 820 in a blood vessel and capture thrombi. The material of struts 824 may be a single material or a combination of materials. The material of struts 824 may be metallic or non-metallic. Stainless steel, titanium, tantalum, and nickel-titanium alloys have all been found to be acceptable metallic materials for struts 824. Preferred non-metallic materials may be selected from the following list, which is not exhaustive: poly(L-lactide) (PLLA), poly(D,L-lactide) (PLA), polyglycolide (PGA), poly(L-lactide-co-D,L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), polyethylene oxide (PEO), polydioxanone (PDS), polycaprolactone (PCL), polyhydroxylbutyrate (PHBT), poly(phosphazene), polyD,L-lactide-co-caprolactone) (PLA/PCL), poly(glycolide-co-caprolactone) (PGA/PCL), polyanhydrides (PAN), poly(ortho esters), poly (phoshate ester), poly(amino acid), poly(hydroxy butyrate), polyacrylate, polyacrylamid, poly(hydroxyethyl methacrylate), polyurethane, polysiloxane and their copolymers.

Struts 824 radiate outwardly from body member 822 such that thrombosis filter 820 is generally conical in shape. When thrombosis filter 820 is deployed inside a blood vessel, free ends 828 engage the blood vessel wall. Body member 822 is held in a position proximate the center of the blood vessel by the plurality of struts 824 which engage the blood vessel walls with opposing force vectors.

The walls of the blood vessel are lined with a thin inner membrane, referred to as an intima or as a thelium. When thrombus filter 820 is implanted in a blood vessel, the thelium is disrupted by free ends 828 of struts 824. When free ends 828 of struts 824 disrupt this inner membrane, the body responds with a process which may be referred to as neointimal hyperplasia, or endothelial growth. As a result of this process, the disrupted area of the thelium is overgrown with a number of new cells.

In a short time, free ends 828 of struts 824 become encapsulated with new cell growth. Due to this endothelial growth, thrombosis filters placed in the blood vessel of a patient become affixed in the blood vessel walls within two weeks after being implanted. Because free ends 828 of struts 824 become fixed to the blood vessel walls in this way, removal of thrombus filter 820 using minimally invasive methods will be difficult if not impossible after it has been in place for more than two weeks.

Applying a coating including a therapeutic substance in a polymeric carrier to thrombosis filter 820 may prevent endothelial growth from encapsulating free ends 828 of struts 824. If encapsulation of free ends 828 of struts 824 is partially or completely prevented, the ability to remove percutaneously remove thrombus filter 820 will be greatly enhanced. The coating including the therapeutic substance may be applied selectively to free ends 828 of struts 824. Alternately, the coating may be applied to substantially all the surfaces of thrombosis filter 820.

When thrombosis filter 820 is disposed in a blood vessel, the conical formation of struts 824 acts to trap, or capture blood clots. The generally conical shape of the formation of struts 824 serves to urge captured blood clots toward the center of the blood flow. The flow of blood around the captured blood clots allows the body's natural lysing process to dissolve the clots. Applying a coating including a therapeutic substance in a polymeric carrier to the vascular filter may assist the body in dissolving blood clots.

A tool 900 which may be used in conjunction with a method of coating thrombosis filter 820 is also shown in FIG. 8. A plurality of gas streams 902 are shown exiting tool 900. In a preferred embodiment, tool 900 is a generally tubular member including a lumen 910 and a plurality of apertures 912. Apertures 912 provide a fluid passage from lumen 910 of tool 900 to the atmosphere surrounding tool 900. Although apertures 912 are illustrated as round holes in FIG. 8, it should be understood that other embodiments of apertures 912 are possible without deviating from the spirit and scope of the invention. For example, apertures 912 may be slots. Lumen 910 of tool 900 is in fluid communication with a supply (not shown) of compressed gas 904. Compressed gas 904 is released to atmosphere through tool 900 to create streams 902.

As was previously mentioned, tool 900 of FIG. 8 may be used in conjunction with a method of applying a polymer coating to thrombosis filter 820. The process begins with the step of preparing a coating solution preferably including a polymer, a solvent, and a therapeutic substance. The coating solution is then applied to thrombosis filter 820 by dipping, spraying, or any other acceptable method. Tool 900 is then used to direct gas streams 902 so that they impinge on the surfaces of thrombosis filter 820. When gas 904 of gas streams 902 strikes the surfaces of thrombosis filter 820, it displaces excess coating solution.

To assure that gas streams 902 impinge upon substantially all the surfaces of thrombosis filter 820, tool 900 may be rotated and moved in a linear direction. Tool 900 may also be moved to a position other than the position shown in FIG. 8 without deviating from the spirit or scope of this invention.

The flow of gas 904 around struts 824 and body member 822 is sufficient to displace excess coating solution. Once the excess coating solution has been removed from or redistributed on the surfaces of thrombosis filter 820, the solvent in the coating solution is allowed to evaporate thereby leaving on the surface of thrombosis filter 820 a polymer coating, which preferably includes a therapeutic agent. Because all imperfections were removed before the coating solution was allowed to dry, the polymer coating resulting from this process is evenly distributed across the surfaces of thrombosis filter 820.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A method for applying a uniform polymeric coating to a medical device, the method comprising the steps of:
   providing a medical device having a plurality of surfaces including at least one internal surface;
   applying a polymeric coating to the plurality of surfaces of the medical device; and
   applying a stream of gas to the plurality of surfaces of the medical device, including the at least one internal surface, wherein the stream of gas is of a sufficient strength to remove excess polymeric coating.

2. The method of claim 1, wherein the stream of gas is applied through an emitting source defining a lumen and at least one aperture in fluid communication with the lumen.

3. The method of claim 2, wherein the at least one aperture is a hole.

4. The method of claim 2, wherein the at least one aperture is a slot.

5. The method of claim 1, wherein the polymeric coating includes a solvent carrier.

6. The method of claim 5, further including the step of evaporating at least a portion of the solvent carrier to form a dried coating.

7. The method of claim 1, wherein the polymeric coating is applied to the surface of the medical device by spraying.

8. The method of claim 1, wherein the polymeric coating is applied to the surface of the medical device by immersing the medical device in the polymeric coating.

9. The method of claim 1, wherein the medical device is a stent.

10. A method for coating an implantable medical device, the method comprising the steps of:
    providing an implantable medical device having a plurality of surfaces, including at least one internal surface;
    coating a polymeric material over the plurality of surfaces of the implantable medical device; and
    applying a stream of gas to the coated surfaces of the implantable medical device, including the at least one internal surface, wherein the stream of gas is of sufficient strength to remove excess polymeric material from the coated surfaces of the implantable medical device.

11. The method of claim 10, whereing the implantable medical device is a stent.

12. The method of claim 10, wherein the stream of gas is applied through an emitting source defining a lumen and at least one aperture in fluid communication with the lumen.

13. The method of claim 12, wherein the at least one aperture is a hole.

14. The method of claim 12, wherein the at least one aperture is a slot.

15. In a process for applying a polymeric material to a medical device having a plurality of surfaces, including at least one internal surface, wherein a coating of polymeric material is applied over the plurality of surfaces of the medical device; the improvement comprising:

applying a stream of gas to the coated plurality of surfaces of the medical device, including the at least one internal surface, wherein the stream of gas is of sufficient strength to remove excess polymeric material from the coated surfaces of the medical device.

16. The process of claim 15, wherein the stream of gas is applied through an emitting source defining a lumen and at least one aperture in fluid communication with the lumen.

17. The method of claim 16, wherein the at least one aperture is a hole.

18. The method of claim 16, wherein the at least one aperture is a slot.

* * * * *

UNITED STATES PATENT AND TRADEMARK OFFICE
CERTIFICATE OF CORRECTION

PATENT NO. : 6,322,847 B1
APPLICATION NO. : 09/685641
DATED : November 27, 2001
INVENTOR(S) : Zhong et al.

It is certified that error appears in the above-identified patent and that said Letters Patent is hereby corrected as shown below:

Title page,
Item [73], Assignee, should read -- SciMed Life Systems, Inc. --.

Signed and Sealed this

Sixth Day of February, 2007

JON W. DUDAS
*Director of the United States Patent and Trademark Office*